(12) United States Patent
Yang

(10) Patent No.: US 6,482,427 B2
(45) Date of Patent: Nov. 19, 2002

(54) COMPOSITIONS AND METHODS FOR REPAIR OF OSSEOUS DEFECTS AND ACCELERATED WOUND HEALING

(75) Inventor: Shih-Liang S. Yang, Laguna Hills, CA (US)

(73) Assignee: Unicare Biomedical, Inc., Laguna Hills, CA (US)

( * ) Notice: Subject to any disclaimer, the term of this patent is extended or adjusted under 35 U.S.C. 154(b) by 0 days.

(21) Appl. No.: 09/814,481

(22) Filed: Mar. 15, 2001

(65) Prior Publication Data

US 2001/0024662 A1 Sep. 27, 2001

Related U.S. Application Data

(63) Continuation-in-part of application No. 09/298,683, filed on Apr. 23, 1999, now Pat. No. 6,228,386.

(51) Int. Cl.$^7$ .................................................. A61F 2/28
(52) U.S. Cl. ........................ 424/426; 523/114; 523/115
(58) Field of Search ........................ 424/426; 523/114, 523/115; 623/16

(56) References Cited

U.S. PATENT DOCUMENTS

| | | | |
|---|---|---|---|
| 3,905,047 A | 9/1975 | Long | |
| 3,981,736 A | 9/1976 | Broemer et al. | |
| 4,131,597 A | 12/1978 | Bluethgen et al. | |
| 4,159,358 A | 6/1979 | Hench et al. | |
| 4,239,113 A | 12/1980 | Gross et al. | |
| 4,563,350 A | 1/1986 | Nathan et al. | |
| 4,608,350 A | 8/1986 | Howard, Jr. | |
| 4,786,555 A | 11/1988 | Howard, Jr. | |
| 4,851,046 A | 7/1989 | Low et al. | |
| 5,141,511 A | 8/1992 | Bauer | |
| 5,204,106 A | 4/1993 | Schepers et al. | |
| 5,658,332 A | 8/1997 | Ducheyne et al. | |
| 5,837,752 A | * 11/1998 | Shastri et al. ............... | 523/116 |

FOREIGN PATENT DOCUMENTS

| | | |
|---|---|---|
| EP | 0 112 319 B1 | 12/1982 |
| EP | 0 145 210 A2 | 10/1983 |
| EP | 0 206 726 B1 | 6/1985 |
| EP | 0 206 726 B2 | 6/1985 |
| EP | 0 206 726 A2 | 6/1985 |
| EP | 0 263 489 B1 | 10/1986 |
| EP | 0 382 047 B1 | 2/1989 |
| EP | 0 394 152 B1 | 4/1989 |
| EP | 0 394 152 A1 | 4/1989 |
| WO | WO 96/000536 | 6/1994 |

OTHER PUBLICATIONS

Kim et al, J. Mater Sci: Mater Med (9) 129, 1998.*
*Bioactive Materials: The Potential for Tissue Regeneration*, Larry L. Hench at Society for Biomaterials 24th Annual Meeting, Apr. 22–26, 1998, San Diego, CA.
*Bonding of Soft Tissues to Bioglass*, J. Wilson & D. Nolletti, CRC Handbook of Bioactive Ceramics, vol. 1, pp. 283–302.
*In–Vivo Study of the Degradation of 4 Different–Composition Active Glasses*, A. M. Gatti, et al. In Bioceramics vol. 8, pp. 41–46.
*Healing of Periodontal Ligament after Implantation of Bio-active Glass in Surgically Created Periodontal Defects: A Pilot Study*, A. M. Gatti, et al. In Bioceramics vol. 7. (Proceedings of the 7th Internat'l. Symposium on Ceramics in Medicine, Turku, Finland, 7/94).
*Bone Growth Into Spaces Between 45S5 Bioglass Granules*, H. Oonishi et al. In Bioceramics vol. 7. (Proceedings of the 7th Internat'l. Symposium on Ceramics in Medicine, Turku, Finland, 7/94).
*Effect of Surface Area to Volume Ratio on in Vitro Surface Reactions of Bioactive Glass Particulates*, D.C. Greenspan et al. In Bioceramics, vol. 7. (Proceedings of the 7th Internat'l. Symposium on Ceramics in Medicine, Turku, Finland, 7/94).
*Bioactive Ceramics: Theory & Applications*, L. L. Hench. In Bioceramics, vol. 7. (Proceedings of the 7th Internat'l. Symposium on Ceramics in Medicine, Turku, Finland 7/94).
*Clinical Applications of Bioglass Implants*, J. Wilson et al. In Bioceramics, vol. 7. (Proceedings of the 7th Internat'l. Symposium on Ceramics in Medicine, Turku, Finland 7/94).

* cited by examiner

Primary Examiner—Carlos Azpuru
(74) Attorney, Agent, or Firm—Stout, Uxa, Buyan & Mullins, LLP; Frank J. Uxa

(57) ABSTRACT

Compositions useful for repairing osseous defects and healing of wounds and burns include particulate bioactive and biocompatible glass including 40 to 58% by weight silica, 10 to 32% by weight calcia, 10 to 32% by weight soda, 2 to 10% by weight phosphorus pentoxide and 0 to 8% by weight silver oxide. The particles have a size distribution of: less than 500 microns. Methods for repairing osseous defects, healing wounds and burns utilizing such compositions are also provided.

37 Claims, No Drawings

COMPOSITIONS AND METHODS FOR REPAIR OF OSSEOUS DEFECTS AND ACCELERATED WOUND HEALING

RELATED APPLICATION

The present application is a continuation-in-part of application Ser. No. 09/298,683, now U.S. Pat. No. 6,228,386, filed Apr. 23, 1999 the disclosure of which is hereby incorporated, in its entirety, herein by reference.

BACKGROUND OF THE INVENTION

The present invention relates to compositions and methods useful for the repair of osseous defects and the accelerated healing of wounds and burns, for example, in various parts of the body of a human or animal. More particularly, the invention relates to compositions including, and methods using such compositions, bioactive, biocompatible glass particles having defined chemical make-ups and particle size distributions, which provide substantial benefits in cost and in the treatment of osseous defects, wounds and burns.

Glass particles have previously been suggested for repairing osseous defects. For example, Low et al U.S. Pat. No. 4,851,046 discloses using glass particles having a broad size distribution of 90 to 710 microns to repair periodontal osseous defects. This patent discloses that a mixture of glass particles having a larger or wider particle size range, including particles having a size range of 500 to 710 microns, might produce a clinically more desirable product. This patent discloses glass particle compositions having a wide overall size distribution and including particles of 500 to 710 microns in size.

Schepers et al U.S. Pat. No. 5,204,106 discloses compositions of glass particles at least 95% by weight of which have sizes between 280 and 425 microns for use in a process for filling an osseous defect or deficiency. This narrow particle size distribution adversely impacts the cost of the product. Moreover, this patent make clear that if the particles are too small, that is smaller than 280 microns, the particles have a tendency to break, and if these particles are present in excessive amounts, that is 5% or more by weight, the desired performance is not achieved. Thus, although the narrow particle size composition is more costly, this patent concludes that such narrow size distribution provides enhanced performance benefits.

Ducheyne et al U.S. Pat. No. 5,658,332 discloses methods for forming osseous tissue in defect sites in the appendicular skeleton or in sites exhibiting reduced metabolic state using glass particles having a size from 200 to 300 microns. This narrow particle size distribution, which is even more narrow than disclosed in the above-noted Schepers et al patent, disadvantageously increases the cost of the product.

It would be advantageous to provide a product, which is effective in repairing osseous defects, meaning to include osseous deficiencies as well, and which is cost effective to produce and use.

Adverse reactions of repairing osseous defect are frequently related to infections associated with biomaterials, which often lead to revision surgery. At present, systemically administered antibiotics, or prophylaxis, is the main defense against bacterial infection following implant surgery. However, antibiotic efficacy is often reduced if the bacteria strains are firmly adherent to the implant materials. In addition, parenteral and oral administration of antibiotics may lead to undesirable side effects by depleting benign microbial flora normally present in the body. Accordingly it would be advantageous to provide a product which is effective in repairing osseous defects, resisting microbial infections and capable of restoring the deficiency or defect site to its original load bearing state.

Particulate bioactive glass is designed to serve as a scaffolding material to encourage cellular growth after implantation. Bioactive glass particles do not show inhibitory actions against bacteria growth under normal physiological conditions.

Since ancient times, silver ion, $Ag^+$, has been used as an antimicrobial agent in treating wounds and broken bones. Silver ion possesses a broad spectrum of antimicrobial action which is suitable for the treatment of infections resulting from polymicrobial colonization on the biomaterials.

The antimicrobial effect of silver-containing ceramics including hydroxyapatite (HA), and bioactive glass have been studied and demonstrated in vitro. For example, Bellantone et al J Biomed Mater Res (51) 484, 2000 disclose a sol-gel derived bioactive glass $SiO_2$-$CaO$-$P_2O_5$-$Ag_2O$ that exhibits a marked bacteriostatic effect on *E. coli* MG1655 without significantly affecting its ability to transform the surface layer of bioactive glass into hydroxy carbonate apatite in vitro. Kim et al J Mater Sci: Mater Med (9) 129, 1998 report that ionic silver in hydroxyapatite possesses antimicrobial effect, while ionic copper and zinc in hydroxyapatite do not exhibit significant antibacterial effect. Cartmell et al J Mater Sci: Mater Med (9) 773, 1998 study the soft tissue response to controlled release glass particulate $Na_2O$-$CaO$-$P_2O_5$-$Ag_2O$ having particle size less than 53 microns and reports that the degrading glass causes tissue necrosis. These studies show that silver ions released from bioceramic exert toxicity toward microbials and might potentially be toxic to tissue as well. The effect of silver ions on the biocompatability of ceramic materials has not been fully studied and/or reported. Silver may form complexes with electron donor groups such as amines, phosphates and thiols by chelation. It has been postulated that silver exerts it toxicity at multiple cellular sites, disrupting the respiratory chain and cell wall synthesis. None of the prior studies address the questions of whether the silver-containing bioceramic is suitable for long-term implantation, and more particularly load bearing function after long term implantation. Silver ion released from bioactive glass may inhibit cellular growth onto and/or into the bioactive glass implant, compromising biocompatability, osseous integration and resulting in implant failure. It is also possible that the implant may exhibit an initial success and later, due to long term accumulation of silver ions, result in implant failure or adverse reactions. Possibly, the long-term failure may not reveal itself until under extreme load bearing conditions.

Glass particles have also been suggested to treat wounds and burns. For example, Greenspan et al U.S. Pat. No. 5,834,008 discloses composition for the accelerated healing of wounds and burns using a mixture of a topical antibiotic and particulate of bioactive glass. This prior art, however, disadvantageously requires that the antibiotic and the particulate bioactive glass be mixed just prior to application in order to minimize reactions between the two components. It would be advantageous to provide a product which is effective in the treatment of wounds and burns without the need to mix a topical antibiotic with the particulate of bioactive glass prior to application.

SUMMARY OF THE INVENTION

New compositions and methods useful to repair osseous defects, and heal wounds and burns, have been discovered. Such compositions provide performance benefits, for example, in terms of effectiveness in repairing osseous defects, in resisting microbial infections and/or in being able to be easily and effectively handled or manipulated prior to such use relative to many of the prior art compositions. In addition, since the present compositions have a relatively broad particle size distribution range, the present compositions are cost effective to produce and use, often more cost effective to produce and use relative to prior art compositions. Moreover, the present compositions can be easily produced and used, for example, employing conventional techniques which are well known in the art.

In one broad aspect of the present invention, compositions useful to repair osseous defects, and heal wounds and burns are provided and comprise particulate bioactive and biocompatible glass. In one embodiment, the present glass particles have the following chemical make-up:

| | |
|---|---|
| Silica | about 40% to about 58% by weight |
| Calcia | about 10% to about 32% by weight |
| Soda | about 10% to about 32% by weight |
| Phosphorus pentoxide | about 2% to about 10% by weight |
| Antimicrobial agent | about 0% or about 0.001% to about 8% by weight |

The antimicrobial agent is present, if at all, in an amount that is in a range of about 0.001%–8%. Preferably, the antimicrobial agent is present in an amount in a range of about 0.01% to about 5% by weight. More preferably, the antimicrobial agent is present in an amount in a range of about 0.010 to about 3% by weight. Still more preferably, the antimicrobial agent is present in an amount in a range of about 0.01% to about 1% by weight.

Preferably, the antimicrobial agent comprises silver. More preferably, the antimicrobial agent comprises silver oxide.

In addition, the particles have the following size distribution:

| | |
|---|---|
| less than about 900 microns | 100% by weight or |
| less than about 700 microns | 100% by weight or |
| less than about 500 microns | 100% by weight |

The particle size distributions set forth herein are based on a measurement using calibrated sieves.

The relatively broad particle size distribution of small and intermediate sized particles, in accordance with the present invention, has been found to provide very effective osseous defect repair, and healing for wounds and burns, to be easily handled or manipulated during use, and to be cost effective to produce, for example, when compared to the compositions of the prior art, as described elsewhere herein. Such findings are indeed surprising since such prior art is directed to compositions which include a broad particle size distribution including particles of about 500 to about 710 microns in size, or to compositions which include very narrow particle size distributions. Moreover, the prior art does not provide a product that exhibits antimicrobial properties. The present compositions are different from these prior art compositions, and provide benefits which are substantial and unexpected from the prior art.

Silver-containing bioactive glass particles, in accordance with the present invention, have been found to exhibit antimicrobial action, to provide very effective osseous defect repair, to restore the repaired site to its original load bearing conditions, to be easily handled or manipulated during use, and to be cost effective to produce. Such findings are surprising since the silver containing bioactive glass particles, in accordance with the present invention, do not show significant opposing effects on biocompatability and osseous integration. Further, it has been surprisingly found that the silver containing particles of bioactive glass, in accordance with the present invention, provide effective wound healing with substantially no adverse reactions and without the need to mix bioactive glass particulate with a topical antibiotic prior to use.

Any and all features described herein and combinations of such features are included within the scope of the present invention provided that the features of any such combination are not mutually inconsistent.

These and other aspects and advantages of the present invention are apparent in the following detailed description and claims.

DETAILED DESCRIPTION OF THE INVENTION

The present compositions include bioactive and biocompatible glass particles including a combination of silica ($SiO_2$), calcia (CaO), soda ($Na_2O$), phosphorus pentoxide ($P_2O_5$) and preferably an antimicrobial agent. Preferably, the antimicrobial agent is silver. More preferably, the antimicrobial agent is silver oxide. Further, such particles have particle size distribution ranging from less than about 1 micron to about 900 microns or more.

As noted previously, in one broad aspect of the invention, the particulate bioactive and biocompatible glass has the following chemical make-up:

| | |
|---|---|
| Silica | about 40% to about 58% by weight |
| Calcia | about 10% to about 32% by weight |
| Soda | about 10% to about 32% by weight |
| Phosphorus pentoxide | about 2% to about 10% by weight |
| Antimicrobial agent | about 0% or about 0.001% to about 8% by weight | and the following particle size distribution:
100% by weight of the particles having a particle size of less than about 900 microns or less than about 700 microns, or less than about 500 microns, or less than about 420 microns, or less than about 350 microns, or less than about 300 microns, or less than about 200 microns or less than about 105 microns.

Measuring particle size distributions using calibrated sieves may result in a limited degree of variation. For example, the sizes of glass particles in the present compositions may vary by an amount of ±1% or less, or ±3% or ±4% or even ±6% of the nominal particle size. Such variations in the nominal sizes of the glass particles of the present compositions are within the scope of the present invention.

In one embodiment, the amount of particles from about 20 microns to less than about 297 microns is about 20% to about 65% by weight.

The present compositions have been found to be very effective in repairing osseous tissue defects (and deficiencies), for example, by implanting the present compositions in such defects.

In addition, the present compositions provide for accelerated healing of burns or wounds, for example, by implanting the present compositions in burns or wounds.

The present compositions exhibit antimicrobial properties and provide for effective bone fill in the osseous defects filled with the compositions. In addition, the speed of bone fill in the defects filled with the present compositions is increased relative to various prior art compositions. Further, excavations are apparent in many of the particles of the present compositions, for example, relative to many of the prior art compositions. As used herein, the term "excavation" is defined as the formation of a central cavity through the interior of a particle at the time of full reaction of the particle which includes gelation and calcium phosphate layer formation. Excavation is evident by observation of cells within a particle. Excavations in a composition are advantageous, for example, to increase the amount of bone fill and the speed of bone fill in an osseous defect implanted with the composition.

The chemical make-up of the glass and/or the particle size distribution may be varied in accordance with the present invention to advantageously provide benefits in the specific application in which the present compositions are used. Such compositions, in general, can be characterized as (A) including small and intermediate sized particles which are often more effective in repairing osseous defects relative to prior art compositions and which are often more cost effective to produce relative to prior art compositions, and/or (B) including an effective amount of an antimicrobial component, preferably silver, to enable antimicrobial action and to reduce and/or eliminate biomaterial-centered infections which are often associated with implant surgeries involving products made according to prior arts.

Preferably, the glass of the present compositions has the following chemical make-up:

| | |
|---|---|
| Silica | about 42% to about 54% by weight |
| Calcia | about 15% to about 29% by weight |
| Soda | about 14% to about 30% by weight |
| Phosphorus pentoxide | about 2% to about 8% by weight |
| Antimicrobial agent | about 0% or about 0.01% to about 6% by weight |

More preferably, the glass has the following chemical make-up:

| | |
|---|---|
| Silica | about 42% to about 48% by weight |
| Calcia | about 20% to about 29% by weight |
| Soda | about 20% to about 28% by weight |
| Phosphorus pentoxide | about 3% to about 8% by weight |
| Antimicrobial agent | about 0% or about 0.01% to about 4% by weight |

Still more preferably, the glass has the following chemical make-up:

| | |
|---|---|
| Silica | about 44% to about 46% by weight |
| Calcia | about 23% to about 26% by weight |
| Soda | about 23% to about 26% by weight |
| Phosphorus pentoxide | about 5% to about 7% by weight |
| Antimicrobial agent | about 0% or about 0.1% to about 3% by weight |

Advantageously the glass has the following chemical make-up:

| | |
|---|---|
| Silica | about 42% to about 54% by weight |
| Calcia | about 15% to about 29% by weight |
| Soda | about 14% to about 30% by weight |
| Phosphorus pentoxide | about 2% to about 8% by weight |
| Antimicrobial agent | about 0% or about 0.01% to about 3% by weight |

An especially useful glass for use in the present compositions has the following chemical make-up:

| | |
|---|---|
| Silica | about 45% by weight |
| Calcia | about 24% by weight |
| Soda | about 25% by weight |
| Phosphorus Pentoxide | about 6% by weight |
| Antimicrobial agent | about 0% or about 0.01% to about 3% by weight |

The presence of trace amounts of certain elements may affect the performance of the present compositions in osseous defect repair applications. For example, trace amounts of certain entities, such as aluminum ion, may prevent the formation of a hydroxy apatite (HA) gel layer on the particle surface. The formation of such a HA layer is believed to be a prerequisite for bone bonding to occur. Also, certain components, such as ferric oxide ($Fe_2O_3$), may cause the particles to disadvantageously discolor by gamma radiation.

Preferably, the trace element concentrations of the present compositions are controlled within relatively stringent limits. In particular, in the present invention no single element, other than these included in the major or primary components of the glasses set forth herein, should be present in the glasses at concentrations of greater than about 0.5% by weight. Thus, it is preferred that the magnesia (MgO) content of the glass be less than about 0.5% by weight, the potassium oxide ($K_2O$) content be less than about 0.5% by weight and the silver oxide (KgO) content be less than about 0.5% by weight. In addition, the amounts of ferric oxide and alumina are less than about 0.5% and about 0.5% by weight, respectively.

In one embodiment, the present compositions preferably include particulate glass including the following sized particles:

| | |
|---|---|
| about 20 microns to less than about 210 microns | about 20% to about 65% by weight |
| about 210 microns to less than about 297 microns | about 20% to about 65% by weight |
| about 297 microns to less than about 350 microns | about 15% to about 55% by weight |
| about 350 microns to less than about 420 microns | about 0% to about 40% by weight |

Preferably, the particulate glass includes the following sized particles:

| | |
|---|---|
| about 20 microns to less than about 210 microns | about 20% to about 60% by weight |
| about 210 microns to less than about 297 microns | about 20% to about 60% by weight |
| about 297 microns to less than about 350 microns | about 20% to about 55% by weight |
| about 350 microns to less than about 420 microns | about 0% to about 40% by weight |

More preferably, the particulate glass includes the following sized particles:

| | |
|---|---|
| about 20 microns to less than about 210 microns | about 20% to about 50% by weight |
| about 210 microns to less than about 297 microns | about 20% to about 50% by weight |
| about 297 microns to less than about 350 microns | about 30% to about 55% by weight |
| about 350 microns to less than about 420 microns | about 10% to about 40% by weight |

In a very useful embodiment, the amount of particles from about 20 microns to less than about 297 microns is in the range of about 20% to about 65% by weight. In one advantageous embodiment, the amount of particles from about 210 to less than about 250 microns is about 20% to about 45% by weight or about 20% to about 40% by weight. The particulate glass may, and preferably does, include substantially no particles less than about 20 microns in size, more preferably substantially no particles less than about 53 microns in size.

In a particularly useful embodiment, the amount of particles from about 297 microns to less than about 350 microns is about 25% to about 40% by weight. More preferably, the amount of particles from about 297 microns to less than about 350 microns is about 28% to about 36% by weight.

Preferably, none to about 40% by weight of the particles have a particle size from about 350 microns to less than about 420 microns. More preferably, none to about 15% by weight of the particles have a size from about 350 microns to less than about 420 microns.

In one embodiment, the particulate glass may, and preferably does, include substantially no particles more than about 420 microns in size.

Very useful compositions in accordance with the present invention comprise particulate bioactive and biocompatible glass having the following chemical make-up:

| | |
|---|---|
| Silica | about 42% to about 54% by weight |
| Calcia | about 15% to about 29% by weight |
| Soda | about 14% to about 30% by weight |
| Phosphorus pentoxide | about 2% to about 8% by weight |
| Antimicrobial agent | about 0.01% to about 3% by weight | and the following particle size distribution:

| | |
|---|---|
| about 20 microns to less than about 210 microns | about 20% to about 50% by weight |
| about 210 microns to less than about 297 microns | about 20% to about 50% by weight |
| about 297 microns to less than about 350 microns | about 30% to about 55% by weight |
| about 350 microns to less than about 420 microns | about 0% to about 25% by weight |

Preferably, the particulate glass includes substantially no particles more than about 420 microns in size.

In a further useful embodiment, compositions in accordance with the present invention comprise particulate bioactive and biocompatible glass having the following chemical make-up:

| | |
|---|---|
| Silica | about 44% to about 46% by weight |
| Calcia | about 23% to about 26% by weight |
| Soda | about 23% to about 26% by weight |
| Phosphorus pentoxide | about 5% to about 7% by weight |
| Antimicrobial agent | about 0.01% to about 2% by weight | and the following particle size distribution:

| | |
|---|---|
| about 20 microns to less than about 210 microns | about 20% to about 40% by weight |
| about 210 microns to less than about 297 microns | about 20% to about 40% by weight |
| about 297 microns to less than about 350 microns | about 30% to about 45% by weight |

In a further useful embodiment, compositions in accordance with the present invention comprise particulate bioactive and biocompatible glass having the following chemical make-up:

| | |
|---|---|
| Silica | about 44% to about 46% by weight |
| Calcia | about 23% to about 26% by weight |
| Soda | about 23% to about 26% by weight |
| Phosphorus pentoxide | about 5% to about 7% by weight |
| Antimicrobial agent | about 0.01% to about 2% by weight | and the following particle size distribution:

| | |
|---|---|
| less than about 105 microns | 100% by weight |

In a preferred embodiment, 100% by weight of the particles are less than 53 microns in size.

The present bioactive, biocompatible glass particles are prepared by melting together the various ingredients. For example, a mixture of powders is prepared including silica, calcium oxide and/or a calcium oxide precursor, a carbonate and/or other sodium oxide precursor for introducing at least a portion of the sodium content, and a phosphate and/or acid phosphate, for example, $CaHPO_4$, for introducing $P_2O_5$, and a silver oxide precursor for introducing at least a portion of the silver content. This mixture is blended and melted, and the molten mixture is poured into liquid water which provides a solidified glass frit.

This glass frit is then ground into particles of approximately the proper size. Using calibrated sieves, for example, in accordance with ASTM method C429-65, the final composition is prepared. The various particle sizes identified herein correspond to specific mesh sizes, for example, as shown in the following:

| Particles size, microns | Sieve size, U.S. mesh |
|---|---|
| 20 | 635 |
| 25 | 500 |
| 32 | 450 |
| 37 | 400 |
| 44 | 325 |
| 53 | 270 |
| 105 | 140 |
| 210 | 70 |
| 250 | 60 |
| 297 | 50 |
| 350 | 45 |
| 420 | 40 |
| 500 | 35 |
| 710 | 25 |

One advantage of the present invention is that a relatively broad range of small and intermediate sized particles are employed in the final compositions. Therefore, the process for producing the present compositions can be specifically designed to achieve a relatively high yield of properly sized particles. In addition, larger sized particles can be recycled to the grinding operation to provide additional particles of the proper size. Overall, a relatively high percentage of the total glass frit produced is ground into properly sized particles for inclusion in the present composition. This reduces the overall cost of the present compositions.

The present compositions may be combined with a solid healing agent. Preferably, the solid healing agent is present in an amount effective to enhance the healing of an osseous defect, burn or wound. In a preferred embodiment, the solid healing agent may be present in the form of a coating on the previously described bioactive, biocompatible glass particles. In one embodiment, the solid healing agent is selected from amorphous calcium phosphates, hydroxyapatite and mixtures thereof. In a preferred embodiment, the solid healing agent comprises hydroxyapatite.

The present compositions may include pharmaceutically acceptable carriers to facilitate application to the wounds, burns and osseous defects. Such pharmaceutically acceptable carriers include those which place the compositions in various forms, such as slurries, pastes, dressings, ointments, gels or liquid suspensions or dispersions and the like. Specific components that may comprise the carriers include, without limitation, white petrolatum, mineral oil, saline, blood, blood components and the like and mixtures and combinations thereof.

The present compositions may be preferably treated with various forms of simulated body fluids include, without limitation, electrolyte solutions, serum solutions and the like and combinations and mixtures thereof, to induce the formation of layers or coatings, for example, superficial hydroxyapatite (HA) layers, hydroxycarbonate apatite (HCA) layers and the like and combinations and mixtures thereof on the surfaces of particulate of bioactive glass prior to application or prior to the introduction of the pharmaceutical carrier for application. The present compositions may be preferably treated with various forms of simulated body fluids, including without limitation, electrolytes solutions, serum solutions, protein solutions and the like and combinations and mixtures thereof, for example, to induce the excavation and the formation of a hollow calcium phosphate shell of particulate bioactive glass prior to application or prior to the introduction of the pharmaceutical carrier for application. A variety of treatment methods and conditions have been reported. The formation of hydroxyapatite, hydroxycarbonate apatite and/or excavation of particulate of bioactive glass may increase the surface area, accelerate tissue regeneration and speed up resorption of particulate bioactive glass after implantation. In addition, the present compositions may include particulate bioactive glass of various shapes and forms, for example, spherical particles, and irregular particles. These specific shapes may preferably be suited for specific applications and/or conditions.

The present invention includes methods for repairing osseous defects, preferably including forming osseous tissue. Such methods comprise implanting a composition in accordance with the present invention in an osseous defect in an amount sufficient to repair such defect. Preferably, such implantation provides, over a period of time, for example, in the range of about 2 weeks to about 3 months or more, for the formation of osseous tissue at the defect site.

Osseous defects which can be repaired using the present compositions include, but are not limited to, cystic defect repairs, tumor or other lesion sites after resection, bone loss defects, fracture sites including delayed or non-union sites, joint repair sites, osteoporosis-related defects, periodontal defects, other defect sites in the appendicular skeleton and the like.

In addition, the present invention includes methods for the treatment of wounds and burns. Such methods comprise contacting a wound with an effective wound-healing amount of the present composition, thereby providing for a release of content of the particulate bioactive glass in the wound.

The following non-limiting examples illustrate certain aspects of the present invention.

EXAMPLE 1

A series of four (4) particulate compositions are selected for testing. Each of the compositions includes particles of bioactive, biocompatible glass having the same chemical make-up as follows:

| | |
|---|---|
| Silica | 45% by weight |
| Calcia | 24.5% by weight |
| Soda | 24.5% by weight |
| Phosphorus pentoxide | 6% by weight |

Each of these compositions has a particle size distribution, determined by calibrated sieves, as follows:

Composition A 210 microns to less than 250 microns - 13% by weight 250 microns to less than 297 microns - 25% by weight 297 microns to less than 350 microns - 32% by weight 350 microns to less than 420 microns - 29% by weight Composition B About 210 microns to less than about 300 microns - 100% by weight Composition C About 300 microns to less than about 350 microns - 100% by weight Composition D About 90 microns to less than about 710 microns - 100% by weight Mature New Zealand white rabbits are implanted with Compositions A to D. Two circular defects of 3 millimeters (mm) in diameter are placed in each ilium of the rabbits. The defects are enlarged gradually to a final diameter of 6 mm and filled with particles of one of the Compositions. Each defect is implanted with material of a singular, randomly selected Composition. Prior to being implanted, the Compositions are wet with three or four drops of sterile physiological saline on a dish. The Compositions are carried from the dish with a flat end spatula and placed in the defect site. All four Compositions form a cohesive mass upon wetting with saline and can be transferred using a spatula with ease. Each rabbit is implanted with all four Compositions. Two rabbits are sacrificed at 3 weeks and at 6 weeks after implantation for histological examination of the repair site.

Block sections of the ilia are excised and embedded in polymethyl methacrylate (PMMA) resin. Four serial sections are obtained from near the center of each defect. The section is stained for observation of the bone, fibrous tissue and glass. The amount of particles exhibiting excavation and the amount of bone fill found in each section are measured using a conventional light microscopy method. The data are compared and rated for each Composition.

Table 1 presents the data from the above study.

TABLE 1

Results of rabbit implantation study

| Rabbit ID | Implant Duration | Composition | Bone fill | Excavation |
|---|---|---|---|---|
| 1, 2 | 3 weeks | A | XXX | XX |
| | | B | XX | X |
| | | C | XX | X |
| | | D | XX | XX |
| 3, 4 | 6 weeks | A | XXXXXX | XXXX |
| | | B | XXXX | XXX |
| | | C | XXXX | XX |
| | | D | XXXXX | XXX |

There is more bone fill in the defects filled with Composition A than those filled with the other Compositions at both 3 weeks and 6 weeks after implantation. Moreover, the speed of bone fill is faster in the defects filled with Composition A than those filled with the other Compositions. Also, more excavations are apparent in the particles of Composition A than in the particles of the other Compositions at 3 weeks and 6 weeks after implantation.

Table 2 compares the ease of manipulating the four Compositions.

TABLE 2

Ease of manipulation

| Composition | Ease of Manipulation | Cohesiveness with saline |
|---|---|---|
| A | Excellent | Excellent |
| B | Excellent | Excellent |
| C | Good | Good |
| D | Excellent | Excellent |

Composition D, which includes particles with a broad size distribution, appears to form a more compact and cohesive mass and is relatively easier to transport.

Composition A is found to be equivalent to or better than the other Compositions in terms of the ease of manipulation.

Clinically, the performance of bond graft materials may be measured by (1) the speed of bone fill and (2) the amount of bone fill. These, in turn, may be affected by (1) pouch formation, (2) packing density, (3) material formulation, (4) particle size, (5) surgical procedures and (6) patient condition.

This study shows that Composition A, in accordance with the present invention, performs as good as or better than the other Compositions, which are representative of prior art materials.

EXAMPLE 2

A series of five (5) particulate compositions are selected for testing. Each of the compositions includes particles of bioactive, biocompatible glass having the following chemical make-up:

| Composition A | |
|---|---|
| Silica | 45% by weight |
| Calcia | 24.5% by weight |
| Soda | 24.5% by weight |
| Phosphorus pentoxide | 6% by weight |
| Compositions B, C | |
| Silica | 45% by weight |
| Calcia | 24% by weight |
| Soda | 24.5% by weight |
| Phosphorus pentoxide | 6% by weight |
| Silver oxide | 0.5% by weight |
| Compositions D, E | |
| Silica | 45% by weight |
| Calcia | 24% by weight |
| Soda | 24% by weight |
| Phosphorus pentoxide | 6% by weight |
| Silver oxide | 1% by weight |

Each of these compositions has a particle size distribution, determined by calibrated sieves, as follows:

Composition A
210 microns to less than 250 microns—13% by weight
250 microns to less than 297 microns—25% by weight
297 microns to less than 350 microns—32% by weight
350 microns to less than 420 microns—29% by weight
Compositions B, D
53 microns to less than 105 microns—100% by weight
Compositions C, E
105 microns to 210 microns—100% by weight The bactericidal effects of silver-containing bioactive glass particles are studied in vitro using a *Pseudomonas aeruginosa* (PA) model. PA is cultured in a Tryptic Soy Broth (TSB) overnight with shaking at 37° C. An aliquot of the PA suspension is diluted with TSB until the optical density at 600 nm is about 1.0. The diluted solution is incubated with shaking for 30 minutes at 37° C. until the optical density of the suspension increases to 1.25 at 600 nm. This working solution (WS) is then serial diluted with TSB (1:100), three times to give solutions WS-1, WS-2 and WS-3.

Transfer and spread 100 ul of WS-3 evenly onto each of two D/E Neutralizing Agar plates (DEA). The plates are cultured overnight in an incubator at 37° C. The colony forming units (CFU) on each plate are counted and found to contain 82 and 78 CFUS, respectively. The average CFU in the original WS is calculated to be $8.0 \times 10^8$ CFU/ml.

Transfer 2.0 ml of TSB, 20 mg of a bioactive glass composition and 20 microliters (ul) of WS into a test tube. The solution in the test tube is incubated at room temperature with shaking for 3 hours. Transfer and mix 20 ul of the resulting suspension with 2.0 ml of D/E Neutralizing Broth (DEB) in a test tube. Spread 100 ul of the resulting suspension evenly onto a DEA plate. The plate is incubated overnight at 37° C. The amount of CFU in the DEA plate is counted and tabulated. The procedures are repeated for each composition of the particulate bioactive glass. The DEA plate is identified according to the composition of the particulate bioactive glass included in the suspension spread and incubated on the plate. For example, DEA (A) and DEA (B) represent plates that are incubated with a suspension Composition A and Composition B of bioactive glass particles, respectively.

PA grows to confluency on DEA (A) plate as would be expected on a plate incubated with working solution only. DEA (B), DEA (C), DEA (D) and DEA (E) plates show scattered CFUs. The average size of each colony on these plates is about half or less than half the average size of the colony on the plate incubated with a working solution only. The data of the CFU counts are listed in Table 1. Based on these data, the reduction of CFU in the solution incubated with bioactive glass particles is calculated and listed in Table 2.

TABLE 1

CFU counts on the DEA plates incubated with solutions containing bioactive glass.

| ID | DEA (B) | DEA (C) | DEA (D) | DEA (E) |
|---|---|---|---|---|
| CFU count | 40 | 920 | 22 | 390 |

TABLE 2

Calculated CFUs in the solutions containing bioactive glass particulate.

| ID | Control | Composition B | Composition C | Composition D | Composition E |
|---|---|---|---|---|---|
| CFU cnt | 80000 | 400 | 9200 | 220 | 3900 |

This study shows that the bactericidal effect of silver-containing bioactive glass depends on the particle size and the silver content of the material. Smaller particles with higher silver concentration increase antibacterial effects. Within the ranges studied, the size of the particle exhibit a significantly greater anti-microbial effect than the concentration of silver in the material. In addition, silver-containing bioactive glass not only significantly decreases the CFU count, but also reduces the size of each individual colony-forming unit. This indicates that the silver-containing bioactive glass is not only bactericidal, but also inhibits the growth of bacteria. Regular bioactive glass shows no antibacterial effect.

EXAMPLE 3

A series of four (4) particulate compositions are selected for testing. Each of the compositions includes particles of bioactive, biocompatible glass having the chemical make-up as follows:

| Compositions A, B | |
|---|---|
| Silica | 45% by weight |
| Calcia | 24.5% by weight |
| Soda | 24.5% by weight |
| Phosphorus pentoxide | 6% by weight |
| Composition C | |
| Silica | 45% by weight |
| Calcia | 24.5% by weight |
| Soda | 24% by weight |
| Phosphorus pentoxide | 6% by weight |
| Silver oxide | 0.5% by weight |
| Composition D | |
| Silica | 45% by weight |
| Calcia | 24% by weight |
| Soda | 24% by weight |
| Phosphorus pentoxide | 6% by weight |
| Silver oxide | 1% by weight |

Each of these compositions has a particle size distribution, determined by calibrated sieves, as follows:

Composition A 210 microns to less than 250 microns—13% by weight 250 microns to less than 297 microns—25% by weight 297 microns to less than 350 microns—32% by weight 350 microns to less than 420 microns'29% by weight Compositions B, C, D 20 microns to less than 150 microns—10% by weight 150 microns to less than 250 microns—26% by weight 250 microns to less than 297 microns—31% by weight 297 microns to less than 350 microns—33% by weight The same protocol described in Example 1 is used in this study. Mature New Zealand white rabbits are implanted with Compositions A to D. Two circular defects are placed in each ilium of the rabbits. Each defect is implanted with material of a singular, randomly selected Composition. Each rabbit is implanted with all four Compositions. The healing is uneventful and there are no untoward reactions at the wound site. Two rabbits are sacrificed at 3 weeks and at 6 weeks after implantation for histological examination of the repair site using the same method as described in Example 1.

Table 1 presents the data from the above study.

TABLE 1

Results of rabbit implantation study

| Rabbit ID | Implant Duration | Composition | Bone fill | Excavation |
|---|---|---|---|---|
| 1, 2 | 3 weeks | A | XXX | XX |
| | | B | XXX | XX |
| | | C | XXX | XX |
| | | D | XX | XX |
| 3, 4 | 6 weeks | A | XXXXX | XXXX |
| | | B | XXXXX | XXX |
| | | C | XXXXX | XXXX |
| | | D | XXXX | XXX |

Table 2 compares the ease of manipulating the four Compositions.

TABLE 2

| | Ease of manipulation | |
|---|---|---|
| Composition | Ease of Manipulation | Cohesiveness with saline |
| A | Excellent | Excellent |
| B | Excellent | Excellent |
| C | Excellent | Excellent |
| D | Excellent | Excellent |

No adverse and/or inflammatory reactions are observed on the wound sites. There are no significant differences in the degree of bone fill and excavation in the defects filled with Composition A through composition D at both 3 weeks and 6 weeks after implantation. All four compositions of bioactive glass particulate are very easy to manipulate and exhibit excellent cohesiveness after mixing with saline.

This study shows that Compositions B, C and D, in accordance with this invention, perform as good as Composition A. Compositions C and D containing small amount of silver, thus imparting antimicrobial effects, do not exhibit untoward, adverse reactions and appear safe, effective and suitable for repairing osseous defects.

EXAMPLE 4

The same four particulate compositions described in Example 3 are employed for testing.

Four young mature racehorses, Hope, Café Café, San Genaro and Santa Ursula are used in this study. These racehorses are disabled due to the presence of an osseous fissure in one of the tibia, a common condition of racehorses. During the surgery, the osseous defect is carefully cleaned and debrided. A round bur is used to remove all soft tissues and create vascular channels in the walls of the defects for intramarrow penetration. Each defect is implanted with material of a singular, randomly selected Composition, as identified in Example 3. Depending on the defect size, about 1 to 1.4 grams of bioactive glass particles, moistened with the horse's blood, are implanted into the defect. The healing is uneventful. There are no untoward reactions at the wound site. All four horses gradually recover and are subjected to rehabilitation, including walking and swimming. Within months after surgery all four horses are able to return to race again. The post-surgery duration for the racehorse to return to race is listed in the following Table.

| | Hope | Café Café, | San Genaro | Santa Ursula |
|---|---|---|---|---|
| Bioactive glass | Composition A | Composition B | Composition C | Composition D |
| Amount used | 1 gram | 1.2 gram | 1.2 gram | 1.4 gram |
| *Duration | 6 months | 5 months | 4 months | 6 months |

Approximate time period between the date of surgery and the date that the horse first returns to race after surgery.

This study demonstrates that the bioactive glass compositions, in accordance with the present invention, are suitable for bone grafting applications to repair osseous defects and to return the subject to normal activities, including extreme load bearing exercises, within a short period of time.

EXAMPLE 5

A particulate bioactive glass composition is selected for testing. The composition has the following chemical makeup:

| Composition | |
|---|---|
| Silica | 45.1% by weight |
| Calcia | 24.2% by weight |
| Soda | 24.5% by weight |
| Phosphorus pentoxide | 6% by weight |
| Silver oxide | 0.2% by weight |

Particle size

Less than 50 microns 5 cc of the above bioactive glass composition is thoroughly mixed with 5cc of a mixture of light mineral oil and white petrolatum. The mixture is directly applied to delayed lesions of about 0.5 cm×0.5 cm of a diabetic foot. These lesions normally remain non-healing for over 14 days. The mixture is applied twice a day. Scar tissue begins to form around the edges of the defect within 2 days. Wound closure and healing is complete within 6 days.

This study demonstrates that the bioactive glass compositions, in accordance with the present invention, are suitable for the accelerated healing of wounds. These wounds may include delayed healing wounds such as lesions suffered by diabetics and burns as a result of exposure to flame or chemicals.

While this invention has been described with respect to various specific examples and embodiments, it is to be understood that the invention is not limited thereto and that it can be variously practiced within the scope of the following claims.

What is claimed is:

1. A composition useful to repair osseous defects, the composition comprising a particulate bioactive and biocompatible glass containing silica and an effective amount of an antimicrobial agent.

2. A composition of claim 1 wherein the antimicrobial agent is present in an amount in a range of about 0.01% to about 8.0% by weight.

3. A composition of claim 1 wherein the antimicrobial agent is present in an amount in a range of about 0.01% to about 5% by weight.

4. A composition of claim 1 wherein the antimicrobial agent is present in an amount in a range of about 0.01% to about 3%. by weight.

5. A composition of claim 1 wherein the antimicrobial agent comprises silver.

6. A composition of claim 1 wherein the antimicrobial agent is silver oxide.

7. A composition according to claim 1 wherein the glass contains soda and has the following particle size distribution:

less than about 900 microns about 100% by weight the particle size distribution being measured using calibration sieves.

8. A composition according to claim 1 wherein the glass has the following particle size distribution:

less than about 700 microns about 100% by weight the particle size distribution being measured using calibration sieves.

9. A composition according to claim 1 wherein the glass has the following particle size distribution:

less than about 500 microns about 100% by weight the particle size distribution being measured using calibration sieves.

10. A composition according to claim 1 wherein the glass has the following chemical makeup:

| | |
|---|---|
| Silica | about 40% to about 58% by weight |
| Calcia | about 10% to about 32% by weight |
| Soda | about 10% to about 32% by weight |
| Phosphorus pentoxide | about 2% to about 10% by weight |
| Antimicrobial agent | about 0.01% to about 8% by weight |

11. A composition of claim 1 which further includes a solid healing component, other than the glass, in an amount effective to enhance healing in an osseous defect into which the composition is placed.

12. A composition of claim 11 wherein the healing component is present in a coating on the glass.

13. A composition of claim 11 wherein the healing component is selected from the group consisting of amorphous calcium phosphate, amorphous hydroxyapatite, crystalline hydroxyapatite, amorphous hydroxycarbonate apatite, crystalline hydroxycarbonate apatite and combinations thereof.

14. A composition useful to repair osseous defects, the composition consisting essentially of:

particulate bioactive and biocompatible glass having the following chemical makeup:

| | |
|---|---|
| Silica | about 40% to about 58% by weight |
| Calcia | about 10% to about 32% by weight |
| Soda | about 10% to about 32% by weight |
| Phosphorus pentoxide | about 2% to about 10% by weight |
| Antimicrobial agent | about 0% to about 8% by weight | and the following particle size distribution:

| | |
|---|---|
| about 20 microns to less than about 210 microns | about 20% to about 65% by weight |
| about 210 microns to less than about 297 microns | about 20% to about 65% by weight |
| about 297 microns to less than about 350 microns | about 15% to about 55% by weight |
| about 350 microns to less than about 420 microns | about 0% to about 40% by weight | the particle size distribution being measured using calibration sieves.

15. A composition of claim 14 wherein the glass has the following sized particles:

| | |
|---|---|
| about 20 microns to less than about 210 microns | about 20% to about 60% by weight |
| about 210 microns to less than about 297 microns | about 20% to about 60% by weight |
| about 297 microns to less than about 350 microns | about 20% to about 55% by weight |

-continued

| | |
|---|---|
| about 350 microns to less than about 420 microns | about 0% to about 40% by weight | the particle size distribution being measured using calibration sieves.

16. A composition of claim 14 wherein the glass has the following sized particles:

| | |
|---|---|
| about 20 microns to less than about 210 microns | about 20% to about 50% by weight |
| about 210 microns to less than about 297 microns | about 20% to about 50% by weight |
| about 297 microns to less than about 350 microns | about 30% to about 55% by weight |
| about 350 microns to less than about 420 microns | about 10% to about 40% by weight | the particle size distribution being measured using calibration sieves.

17. A composition of claim 14 wherein the glass has the following sized particles:

| | |
|---|---|
| about 20 microns to less than about 53 microns | about 0% to about 40% by weight |
| about 53 microns to less than about 105 microns | about 0% to about 40% by weight |
| about 105 microns to less than about 210 microns | about 20% to about 65% by weight | the particle size distribution being measured using calibration sieves.

18. A composition of claim 14 wherein the glass has the following sized particles:

| | |
|---|---|
| about 20 microns to less than about 53 microns | about 0% to about 40% by weight |
| about 53 microns to less than about 105 microns | about 10% to about 40% by weight |
| about 105 microns to less than about 210 microns | about 10% to about 55% by weight | the particle size distribution being measured using calibration sieves.

19. A composition of claim 14 wherein the glass has the following chemical make-up:

| | |
|---|---|
| Silica | about 44% to about 46% by weight |
| Calcia | about 23% to about 26% by weight |
| Soda | about 23% to about 26% by weight |
| Phosphorus pentoxide | about 5% to about 7% by weight |
| Antimicrobial agent | about 0% to about 3% by weight |

20. A composition of claim 14 which further includes a solid healing component, other than the glass, in an amount effective to enhance healing in an osseous defect into which the composition is placed.

21. A composition of claim 20 wherein the healing component is present in a coating on the glass particulate.

22. A composition of claim 20 wherein the healing component is selected from the group consisting of amorphous calcium phosphate, amorphous hydroxyapatite, crystalline hydroxyapatite, amorphous hydroxycarbonate apatite, crystalline hydroxycarbonate apatite and combinations thereof.

23. A composition useful for the healing of wounds and burns, the composition comprising a particulate bioactive and biocompatible glass containing silica and an effective amount of an antimicrobial agent.

24. A composition of claim 23 wherein the antimicrobial agent is present in an amount in a range of about 0.0% to about 8.0%.

25. A composition of claim 23 wherein the antimicrobial agent is present in an amount in a range of about 0.01% to about 3% by weight.

26. A composition of claim 23 wherein the antimicrobial agent is present in an amount in a range of about 0.01% to about 1% by weight.

27. A composition of claim 23 wherein the antimicrobial agent comprises silver.

28. A composition of claim 23 wherein the antimicrobial agent is silver oxide.

29. A composition according to claim 23 wherein the glass has the following particle size distribution:

| | |
|---|---|
| less than about 105 microns | about 100% by weight | the particle size distribution being measured using calibration sieves.

30. A composition according to claim 23 wherein the glass has the following particle size distribution:

| | |
|---|---|
| less than about 200 microns | about 100% by weight | the particle size distribution being measured using calibration sieves.

31. A composition of claim 24 wherein the glass has the following chemical make-up:

| | |
|---|---|
| Silica | about 40% to about 58% by weight |
| Calcia | about 10% to about 32% by weight |
| Soda | about 10% to about 32% by weight |
| Phosphorus pentoxide | about 2% to about 10% by weight |
| Antimicrobial agent | about 0.01% to about 8% by weight |

32. A composition of claim 24 which further includes a solid healing component, other than the glass, in an amount effective to enhance healing in an osseous defect into which the composition is placed.

33. A composition of claim 32 wherein the healing component is present in a coating on the glass particulate.

34. A composition of claim 32 wherein the healing component is selected from the group consisting of amorphous calcium phosphate, amorphous hydroxyapatite, crystalline hydroxyapatite, amorphous hydroxycarbonate apatite, crystalline hydroxycarbonate apatite and combinations thereof.

35. A composition of claim 24 further comprising a pharmaceutically acceptable carrier.

36. A composition of claim 35 wherein the pharmaceutically acceptable carrier is selected from the group consisting of dressing, liquid media, slurries, pastes, ointments, gels and combinations thereof.

37. A composition of claim 35 wherein the pharmaceutically acceptable carrier comprises an agent selected from the group consisting of white petrolatum, mineral oil, saline, blood, blood components and combinations thereof.

* * * * *

UNITED STATES PATENT AND TRADEMARK OFFICE
CERTIFICATE OF CORRECTION

PATENT NO. : 6,482,427 B2  Page 1 of 1
APPLICATION NO. : 09/814481
DATED : November 19, 2002
INVENTOR(S) : Yang It is certified that error appears in the above-identified patent and that said Letters Patent is hereby corrected as shown below:

<u>Column 3</u>

Line 47, "0 . 010" should read --0 . 01%-- .

<u>Column 15</u>

Line 32, "microns ' 29%" should read --microns - 29%-- .

<u>Column 16</u>

Line 32, "Café Caf6" should read --Café Café-- .

<u>Column 20</u>

Line 11, "0 . 0%" should read --0 . 01%-- .

Signed and Sealed this

Twenty-seventh Day of November, 2007

JON W. DUDAS
*Director of the United States Patent and Trademark Office*